United States Patent [19]

Yamaguchi et al.

[11] Patent Number: 4,871,442
[45] Date of Patent: Oct. 3, 1989

[54] ION SENSOR

[75] Inventors: Shuichiro Yamaguchi, Fuji; Norio Daikuhara; Takeshi Shimomura, both of Fujinomiya, all of Japan

[73] Assignee: Terumo Corporation, Tokyo, Japan

[21] Appl. No.: 44,062

[22] Filed: Apr. 29, 1987

[30] Foreign Application Priority Data

May 1, 1986 [JP] Japan .................................. 61-101724
May 13, 1986 [JP] Japan .................................. 61-109128
May 26, 1986 [JP] Japan .................................. 61-120564

[51] Int. Cl.$^4$ .......................................... G01N 27/30
[52] U.S. Cl. ..................................... 204/418; 204/416
[58] Field of Search ................................ 204/416–419

[56] References Cited

U.S. PATENT DOCUMENTS

| | | | |
|---|---|---|---|
| 3,598,713 | 8/1971 | Baum et al. | 204/418 |
| 3,932,233 | 1/1976 | Ruzicka | 204/418 |
| 4,052,285 | 10/1977 | Dobson | 204/195 |
| 4,115,209 | 9/1978 | Fraiser et al. | 204/418 |
| 4,198,851 | 4/1980 | Janata | 73/23 |
| 4,214,968 | 7/1980 | Battaglia et al. | 204/418 |
| 4,280,889 | 7/1981 | Szonntagh | 204/195 |
| 4,282,079 | 8/1981 | Chang et al. | 204/420 |
| 4,282,099 | 8/1981 | Chang et al. | 204/195 G |
| 4,305,802 | 12/1981 | Koshiishi | 204/195 |
| 4,454,007 | 6/1984 | Pace | 204/1 T |
| 4,502,938 | 3/1985 | Covington et al. | 204/418 |
| 4,512,870 | 4/1985 | Kohara et al. | 204/416 |
| 4,549,951 | 10/1985 | Knudson et al. | 204/416 |
| 4,561,962 | 12/1985 | Kankare | 204/418 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/1 T |

FOREIGN PATENT DOCUMENTS

| | | |
|---|---|---|
| 0056283 | 7/1982 | European Pat. Off. |
| 167126 | 1/1986 | European Pat. Off. |
| 186210 | 7/1986 | European Pat. Off. |
| 57-196116 | 12/1982 | Japan |
| 0167951 | 10/1983 | Japan .................................. 204/416 |
| 85167951 | 10/1983 | Japan .................................. 204/416 |
| 59-571556 | 4/1984 | Japan |
| 59-142451 | 8/1984 | Japan |
| 60-7357 | 1/1985 | Japan |
| 898314 | 1/1982 | U.S.S.R. .................................. 204/418 |
| 0898314 | 1/1982 | U.S.S.R. .................................. 204/418 |

OTHER PUBLICATIONS

Tamura et al, "Coated Wire Sodium- and Potassium-Selective Electrodes Based on Bis(crown ether) Compounds", Analytical Chemistry, vol. 54, No. 7, Jun. 1982, pp. 1224–1227.

Wuthier et al, "Tin Organic Compounds as Neutral Carriers for Anion Selective Electrodes", Analytical Chemistry, vol. 56, No. 3, Mar. 1984, pp. 535–538.

Norov et al, "Calcium-Selective Electrode Without an Internal Reference Solution", Journal of Analytical Chemistry, vol. 34, No. 8, Part 1, Aug. 1979, pp. 1159–1162.

Oyama et al, "Ion Selective Electrodes Prepared by Modifying an Electrode With Polymers", Tokyo Seminar on Macromolecule-Metal Complexes, Tokyo Univ, Oct. 14–17, 1987.

Oyama et al, "Hydrogen Ion Selective Microlectrode Prepared by Modifying an Electrode With Polymers", Analytical Chemistry, 1987, vol. 59, pp. 258–262.

Oyama et al, "Hydrogen Ion Selective Microlectrode Prepared by Modifying an Electrode With Polymers", International Electroanalytical Symposium, Schaumberg, Ill., May 27–29, (1987), pp. 122–125.

Oyama et al, "A New Type of Ion-Selective Microelectrodes Using Electropolymerized Thin Films", j-4 Bioelectroanalytical Chemistry Symposium, Honolulu, Hi., Oct. 18–23, 1987.

Primary Examiner—John F. Niebling
Assistant Examiner—Kathryn Gorgos
Attorney, Agent, or Firm—Burns, Doane, Swecker & Mathis

[57] ABSTRACT

An ion sensor includes an electrically conductive substrate, a redox layer coating the surface of the electrically conductive substrate, a barrier layer coating the surface of the redox layer, and an ion-selective layer coating the surface of the barrier layer. The barrier layer functions to prevent migration between the ion-selective layer and redox layer of substances constituting these layers, and to transmit a potential difference produced in the ion-selective layer by contact with an ion from the ion-selective layer to the redox layer.

23 Claims, 2 Drawing Sheets

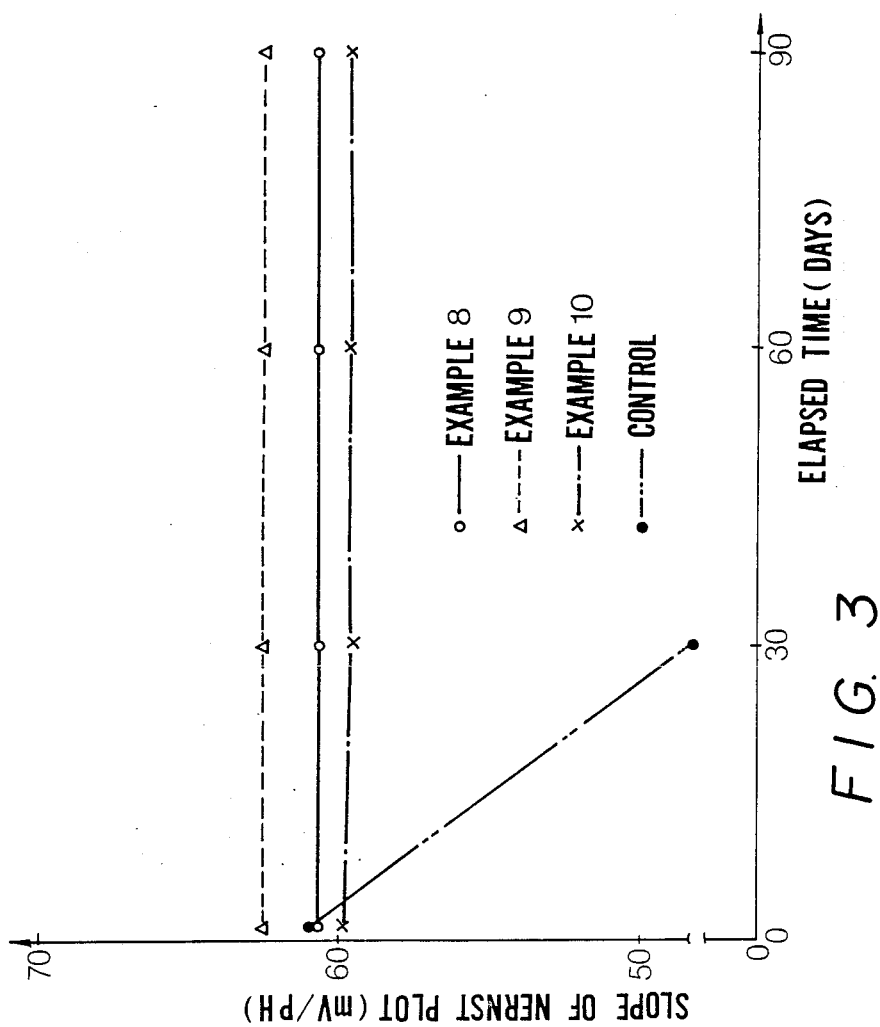

ION SENSOR

BACKGROUND OF THE INVENTION

1. Field of the Invention

This invention relates to an ion sensor for measuring the ionic concentration of a solution by the potentiometric response of an electrode. More particularly, the invention relates to a solid-state ion sensor devoid of an internal (standard) solution, especially an ion sensor capable of measuring ionic concentration in vivo.

2. Description of the Prior Art

An ion sensor most commonly used in the prior art is constituted by a glass membrane electrode. However, the glass membrane in such an electrode breaks easily, and frequent washing is necessary since measurements taken thereby are influenced by the existence of interfering ions, medicines, the proteins in a living body, amino acids and trace amounts of active ingredients. These and other inconveniences are encountered in terms of use.

Recently, pH electrodes using a polymeric membrane have recently been reported as an improvement on the glass membrane electrode. For example, a liquid membrane electrode is described in Analytical Chimica Acta, 131, (1981), pp. 111≅116, and a solid membrane electrode is disclosed in Japanese Patent Application No. 59-281076. However, since these electrodes possess an internal liquid chamber just as the glass membrane electrode, they do not fundamentally solve the problems of the glass electrode and are not fully satisfactory.

However, ionic concentration measurements for clinical examinations and the like are now being performed under increasingly harsh conditions. In addition to the ability to perform measurements precisely, these sensors must have characteristics that (1) enable ionic concentration measurements to be performed continuously and (2) enable ionic concentration measurements to be performed accurately even if there is a sudden change in temperature.

Membrane-coated solid-state electrodes can be made very small. They also do not have an internal liquid chamber and, hence, there is no risk of an internal liquid leaking and contaminating a specimen undergoing measurement. For these reasons, electrodes of this type are attracting considerable interest since they are well-suited for use as clinical sensors.

SUMMARY OF THE INVENTION

A solid-state, compact sensor for measuring the ionic concentration of a liquid based on the potentiometric response of an electrode has been proposed in Japanese Patent Application No. 60-290812 and comprises an electrically conductive substrate, a redox layer deposited on the substrate, and an ion-selective layer coating the surface of the redox layer. However, it has been found that since the redox layer composition dissolves into the ion-selective layer, the ionic characteristics of the electrode, particularly the ionic sensitivity thereof, deteriorate after about one month.

Accordingly, an object of the present invention is to provide an ion sensor in which a redox layer composition and ion-selective layer composition will not undergo mutual dissolution or elution, thereby affording stable ionic characteristics over an extended period of time, a high selectivity to interfering ions and a high speed of ionic response.

According to the present invention, the foregoing object is attained by providing an ion sensor comprising an electrically conductive substrate, a redox layer coating a surface of the electrically conductive substrate, a barrier layer coating a surface of the redox layer, and an ion-selective layer coating a surface of the barrier layer, the barrier layer functioning to prevent migration between the ion-selective layer and redox layer of substances constituting these layers, and to transmit a potential difference produced in the ion-selective layer by contact with an ion from the ion-selective layer to the redox layer. In a preferred embodiment, the barrier layer has a thickness of 0.2 $\mu$m–1.0 mm.

In accordance with the invention, the provision of the barrier layer between the redox layer and ion-selective layer prevents the compositions of these two layers from undergoing mutual dissolution and elution, so that the ionic characteristics of the sensor, namely the slope of the Nernst plot thereof, do not change over an extended period of time. Provision of the barrier layer also raises selectivity with respect to interfering ions and quickens the speed of ionic response.

By adopting a barrier layer thickness of 0.2 $\mu$m–1.0 mm, temperature characteristics can be obtained similar to those of a conventional glass electrode having an internal liquid chamber. Measurements can be taken over a pH range of 6.0–8.0, which is substantially the range encountered in a living body, with no temperature dependence between 20° C. and 45° C.

Since the ion sensor of the invention is a solid-state sensor different from a glass electrode having an internal liquid chamber, the sensor is easy to handle and can be made small in size. Morever, since the sensor of the invention is not readily breakable, unlike the glass electrode, it can be combined with a guide wire, catheter or the like and employed as a clinical ion sensor to measure ions in vivo.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 3 is a plot showing the results of experiments conducted using hydrocarbon ion sensors embodying the present invention.

DESCRIPTION OF THE PREFERRED EMBODIMENT

Figure 2:
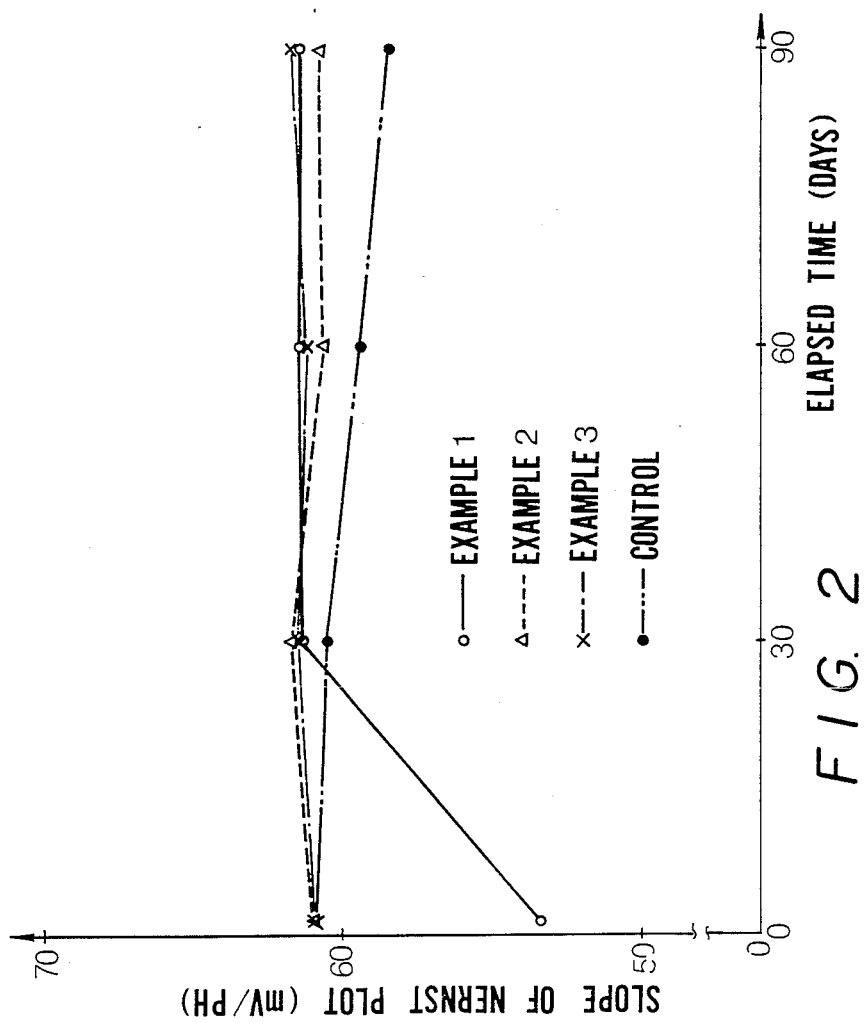
FIG. 2 a plot showing the results of experiments conducted using hydrogen ion sensors embodying the present invention.

The present invention will now be described in detail on the basis of embodiments thereof. The features of the invention will become clear from the following description taken in conjunction with FIGS. 1 through 3 and Tables 1 through 4.

Figure 1:
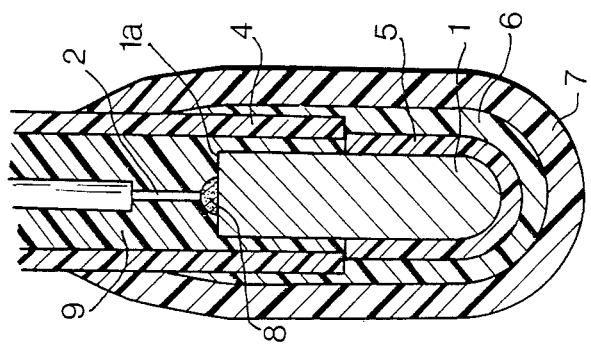
FIG. 1 is a longitudinal sectional view illustrating an ion sensor in accordance with the present invention.

FIG. 1 is a longitudinal sectional view of an ion sensor according to the invention.

<Formation of Redox Layer>

A lead wire 2 consisting of Teflon-coated copper wire having a diameter of 0.2 mm is fixed by means of an electrically conductive adhesive 8 to the bottom surface 1a of an electrically conductive substrate 1 having a diameter of 1.1 mm and a length of 3.0 mm. The outer periphery of the electrically conductive substrate 1 is sheathed and insulated by heat-shrinkable tubing 4 via an insulative layer 9 so as to leave the tip of the substrate exposed to a length of 1.5 mm. The exposed tip of the electrically conductive substrate 1 is ground and polished into a hemispherical shape, with the surface area of the exposed portion being adjusted to 0.064 cm². A redox layer 5 is formed on the exposed surface of the substrate 1 by electrolytic oxidative polymerization. Thus is formed an electrode (hereinafter referred to as a "redox electrode") having the redox layer 5 covering the electrically conductive substrate 1.

The electrically conductive substrate used in the ion sensor of the invention may consist of an electrically conductive carbon material such as basal-plane pyrolytic graphite (hereafter referred to as "BPG") or glassy carbon, a metal such as gold, platinum, copper, silver, palladium, nickel or iron, especially a precious metal, or a composite obtained by coating the surface of any of these metals with a semiconductor such as indium oxide or tin oxide. The electrically conductive carbon material is preferred, especially BPG. In order to make the conductive substrate small in size, a stick-shaped member is used and a membrane having a redox function is deposited over an area of 1–20 mm² on the outer circumferential surface of the stick-shaped substrate or on its outer circumferential surface and tip surface. A lesser area is undesirable as it will cause the electrode membrane resistance of the ion carrier membrane to exceed 50 MΩ at 10° C.; a larger area will result in an ion sensor which is no longer small in size. Though the stick-shaped substrate may be of a cylindrical, prismatic or like configuration, the cylindrical substrate having a rounded tip is especially preferred in terms of moldability and membrane adhesion. Conventionally, the basal plane of BPG is utilized as the electrode plane. However, the inventor has discovered that the edge plane of BPG can also be effectively exploited, and that because of this, a stick-shaped electrode can be fabricated even from BPG. BPG is highly preferred since it excels in terms of sensor operating stability. A stick of BPG, for example of the cylindrical shape, will exhibit excellent strength especially if the diameter selected is 0.1–2 mm.

The redox layer refers to one in which an electrode comprising an electrically conductive substrate having this layer deposited on its surface is capable of generating a constant potential on the substrate owing to a redox reaction. In the present invention, an especially preferred redox layer is one which will not allow the potential to fluctuate due to the partial pressure of oxygen gas. Particularly suitable examples of the redox layer are (1) an organic compound membrane or a polymeric membrane capable of a quinone-hydroquinone type redox reaction, (2) an organic compound membrane or polymeric membrane capable of an amine-quinoid type redox reaction, and (3) poly (pyrrole) and poly (thionylene) compound type electro conductive substrates. The quinone-hydroquinone type redox reaction is expressed by e.g. the following reaction formula, taking a polymer as an example:

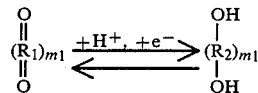

where $R_1$, $R_2$ represent e.g. compounds having a structure containing an aromatic series.

The amine-quinoid type redox reaction is expressed by e.g. the following reaction formula, taking a polymer as an example:

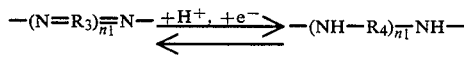

where $R_3$, $R_4$ represent e.g. compounds having a structure containing an aromatic series.

The following compounds (a)–(d) can be mentioned as compounds capable of forming the above mentioned layer having the redox function:

(a) A hydroxy aromatic compound expressed by

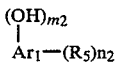

where $Ar_1$ represents an aromatic nucleus, $R_5$ a substituent group, $m_2$ is 1 to the effective valence of $Ar_1$, and $n_2$ is 0 to the effective valence of $Ar_1$ minus 1.

The aromatic nucleus of $Ar_1$ may be a single ring such as a benzene nucleus, a multiple ring such as an anthracene nucleus, pyrene nucleus, chrysene nucleus, perylene nucleus or coronene nucleus, or a heterocyclic ring. Examples of the substituent group $R_5$ are alkyl groups such as a methyl group, aryl groups such as a phenyl group, and a halogen atom. More specifically, examples are dimethyl phenol, phenol, hydroxy pyridine, o- and m-benzyl alcohols, o-, m- and p-hydroxybenzaldehydes, o- and m-hydroxyacetophenones, o-, m- and p-hydroxypro-piophenons, o-, m- and p-hydroxybenzophenones, o-, m- and p-carboxyphenols, diphenlphenol, 2-methyl-8-hydroxy-quinoline, 5-hydroxy-1, 4-naphthoquinone, 4-(p-hydroxy-phenyl)2-buthanone, 1,5-dihydroxy-1,2,3,4-tetra-hydronaphthalene, bisphenol-A, salicylanilide, 5- and 8-hydroquinolines, 1,8-dihydroxyanthraquinone, and 5-hydroxy-1,4-naphthoquinone (b) An amino aromatic compound expressed by the formula

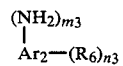

where $Ar_2$ represents an aromatic nucleus, $R_6$ a substituent group, $m_3$ is 1 to the effective valence of $Ar_2$, and $n_3$ is 0 to the effective valence of $Ar_2$ minus 1.

As for the aromatic nucleus $Ar_2$ and the substitution group $R_6$, items similar to $Ar_1$ and the substitution group $R_5$ in compound (a) can be used. Specific examples of the amino aromatic compound are aniline, 1,2-diaminobenzene, aminopyrene, diaminopyrene, aminochrysene, diaminochrysene, 1-aminonaphtholene, 9-aminonaphtholene, 9, 10-diaminonaphtholene, 1-aminoanthraquinone, p-phenoxyaniline, o-phenylenediamine, p-chloroaniline, 3,5-dichloroaniline, 2,4,6-trichloroaniline, N-methylaniline, and N-phenyl-p-phenylenediamine and so on.

(c) A quinone such as 1,6-pyrenequinone, 1,2,5,8-tetrahydroxynalizaline, phenanthrenequinone, 1-aminoanthraquinone, purpurine, 1-amino-4-hydroxyanthraquinone, and anthralphyne.

Among these compounds, 2,6-xylenol and 1-aminopyrene are especially preferred.

(d) Pyrrole and derivatives thereof (e.g. N-methyl pyrrole), and thiophene and derivatives thereof (e.g. methyl thiophene).

Further, examples of compounds capable of forming the layer having the redox function are those which undergo a redox reaction. The following can be mentioned: poly(N-methyl aniline) [Onuki, Matsuda, Oyama, Nihon Kagakukaishi, 1801–1809 (1984)], poly(2,6-dimethyl-1,4-phenylene ether), poly(o-phenylediamine), poly(phenol) and polyxylenol; organic compounds containing the compounds (a) through (d) such as pyrazoroquinone group-containing vinyl compound-polymers, isoaroxythazine group-containing vinyl compound-polymers and other quinone group-containing compound-polymers, lower polymeric compounds (oligomers) of compounds (a) through (d), or substances obtained by fixing the compounds of (a) through (d) to polymeric compounds such as polyvinyl compounds and polyamide compounds. In the present specification, the term "polymer" is taken to mean both homopolymers and mutual polymers such as copolymers.

In the present invention, in order to deposit the compound capable of forming the redox layer on the an electrically conductive substrate, a polymer obtained by synthesizing an amino aromatic compound, a hydroxy aromatic compound or the like on an electrically conductive substrate of electrically conductive carbon or a precious metal by an electrolytic oxidation polymerization method or electrodeposition method, or a polymer synthesized by application of electron beam irradiation, light or heat, is dissolved in a solvent. The resulting solution is (a) deposited on electrically conductive substrate by painting or dipping, (b) reacted in the gas phase in vacuo and deposited directly on the an electrically conductive substrate, or (c) irradiated with light, heat or radiation to be deposited directly on the electrically conductive substrate. Among these three methods, the most preferred is that in which, electrooxidation polymerization method. The electrolytic oxidation polymerization method is implemented by subjecting the amino aromatic compound or hydroxy aromatic compound to electrolytic oxidation polymerization in a solvent in the presence of a suitable supporting electrolyte and depositing a layer of the polymer on the surface of the electrically conductive substrate. Preferred examples of the solvent are acetonitrile, water, dimethyl formamide, dimethyl sulfoxide, propylene carbonate, methanol and the like. Preferred examples of the supporting electrolyte are sodium perchlorate, sulfuric acid, sodium sulfate, phosphoric acid, boracic acid, tetraofluoro-potassium phosphate, quaternary ammonium salts and the like.

The membrane thickness of the redox layer is 0.01 $\mu$m–1.0 mm, preferably 0.1 $\mu$m–0.1 mm. A membrane thickness of less than 0.01 $\mu$m does not fully bring forth the effects of the invention, while a thickness of more than 1.0 mm is undesirable from the viewpoint of miniaturizing the sensor.

The redox layer used in the present invention can be used in a form impregnated with an electrolyte. Examples of the electrolyte are phosphoiic acid, dipotassium hydrogen phosphate, sodium perchlorate, sulfuric acid, tetrafluoro borate, tetraphenyl borate and the like. In order to impregnate the redox layer with the electrolyte, a simple method which can be adopted is to coat the electrically conductive substrate with the redox layer and then dip the resulting membrane into a solution of the electrolyte.

<Formation of Barrier Layer>

The outer surface of the redox electrode is coated with a barrier layer 6, which functions to prevent migration between the redox layer 5 and an ion-selective layer 7, described below, of substances constituting these layers, and to transmit a potential difference produced in the ion-selective layer 7 by contact with an ion from the ion-selective layer 7 to the redox layer 5.

A preferred example of the barrier layer having the functions described above is a polymeric layer possessing an electrolytic solution or aqueous solution, with a gelled polymeric layer being particularly preferred. Preferred examples of such polymeric layers are a layer of a cellulose derivative such as polyvinyl alcohol (PVA) or acetyl cellulose, a natural aqueous polymeric layer such as gelatin or agar-agar, or a semisynthetic aqueous polymeric layer such as mannan or starch. Among these, PVA is especially preferred.

Coating the redox layer with the barrier layer is accomplished by e.g. preparing a 10% aqueous solution of PVA or a 10% aqueous solution of PVA containing an electrolyte, dipping the redox electrode in this solution sufficiently, lifting the electrode from the solution, blow-drying the electrode and then drying it at 150° C. These steps are repeated to adjust the barrier layer to the desired thickness. A pH buffer solution is preferred as the electrolytic solution, with a citrate or phosphate solution being preferred for sensing hydrogen ion. As for the pH range, 4.8–7.4, which is approximately the same as the pH in a living body, is preferred, especially a range of 6.0–7.4. The thickness of the PVA layer should be 0.2 $\mu$m–1.0 mm, preferably 200 $\mu$m–800 $\mu$m. The thickness most preferred is 400 $\mu$m–600 $\mu$m.

<Formation of Ion-Selective Layer>

A layer in which an ion carrier substance for the ion of interest and, if necessary, an electrolyte, are carrier on a polymeric compound is used as the ion-selective layer 7 coating the surface of the barrier layer 6.

The following are examples of the ion carrier material which can be used, depending upon the ion of interest:

(i) For hydrogen ion

Examples of a hydrogen ion carrier material are amines expressed by the formula

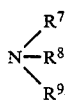

(where $R^7$, $R^8$, $R^9$ represent the same or different alkyl groups, among which at least two alkyl groups have a carbon number of 8–18), and compounds expressed by the formula

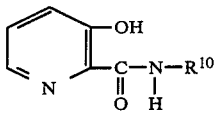

(where $R^{10}$ represents an alkyl group having a carbon number of 8–18). Tri-n-dodecylamine is especially preferred.

(ii) For potassium ion

Examples of which can be mentioned are valinomycin, nonactin, monactin, crown ether compounds such as dicyclohexyl-18-crown-6, naphtho-15-crown-5, bis(15-crown-5) and the like. Among these, valinomycin and bis(15-crown-5) are ideal.

(iii) For sodium ion

Examples which can be mentioned are aromatic amides or diamides, aliphatic amides or diamides, and crown compounds, e.g. bis[(12-crown-4)methyl]-dodecylmalonate, N,N,N,N-tetrapropyl-3,6-dioxanate diamide, N,N,N',N'-tetrabenzyl-1,2-ethenedioxydiacetoamide, N,N'-dibenzyl-N,N'-diphenyl-1,2-phenylenediacetoamide, N,N',N''-triheptyl-N,N'N''-trimethyl-4,4',4''-propyridine tris(3-oxythabutylamide), 3-methyoxy-N,N,N,N-tetrapropyl-1,2-phenylene dioxydiacetoamide, (−)-(R,R)-4,5-dimethyl-N,N,N,N-tetrapropyl-3,6-dioxaoctanediamide, 4-methyl-N,N,N,N-tetrapropyl-3,6-dioxaoctane diamide, N,N,N,N-tetrapropyl-1,2-phenylenedioxydiacetoamide, N,N,N,N-tetrapropyl-2,3-naphthanedioxydiacetoamide, 4-t-butyl-N,N,N,N-tetrapropyl-1,2-dicyclohexanedioxydiacetoamide, cis-N,N,N,N-tetrapropyl-1,2-cyclohexanedioxydiacetoamide, and trans-N,N,N,N-tetrapropyl-1,2-cyclohexanedioxydiacetoamide. Among these, bis[(12-crown-4) methyl]dodecylmalonate is well-suited for use.

(iv) For chloride ion

Examples which can be mentioned are quaternary ammonium salts expressed by the formula

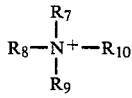

(where $R^7$, $R^8$, $R^9$ represent the same or different alkyl groups having a carbon number of 8–18, and $R^{10}$ represents hydrogen or an alkyl group having a carbon number of 1–8, and a triphenyl tin chloride expressed by the formula

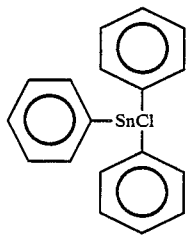

(v) For calcium ion

Suitable examples are bis[di-(n-octylphenyl) phosphate], (−)-(R,R)-N,N'-bis[(11-ethoxycarbonyl) undecyl]-N,N',4,5-tetramethyl-3,6-dioxaoctanediamide and calcium bis[di(n-decyl) phosphate].

(vi) For hydrogencarbonate ion

Examples which can be mentioned are a quaternary ammonium salts expressed by the formula

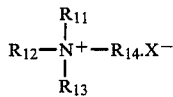

(where $R_{11}$, $R_{12}$, $R_{13}$ represent the same or different alkyl groups having a carbon number of 8–18, $R_{14}$ represents hydrogen atom or an alkyl group having a carbon number of 1–4, and $X^-$ represents $Cl^-$, $Br^-$ or $OH^-$), tertiary amine compounds expressed by the formula

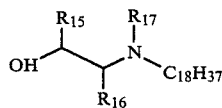

(where $R_{15}$ represents a phenyl group, hydrogen atom or a methyl group, $R_{16}$ represents hydrogen atom or a methyl group, and $R_{17}$ represents a methyl group or an octadecyl group), and a compound expressed by the formula

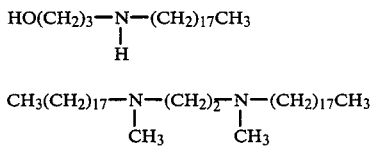

(vii) For ammonium ion

Suitable example are nonachtine+monachtine, tetranactine, etc.

Examples of the electrolytic salt are sodium tetrakis(p-chlorophenyl) borate, potassium tetrakis(p-chlorophenyl) borate, and a compound expressed by the formula $(R_{18})_4NBF_4$ where $R_{18}$ represents an alkyl group, preferably an alkyl group having a carbon number of 2–6.

Potassium tetrakis (p-chlorophenyl) borate is especially suited for use to hydrogen ion, potassium ion, sodium ion and hydrogencarbonate ion. eetrachloroborate is to chlorine ion. Di-(n-octylphenyl) phosphate is to calcium ion.

Examples of the polymer compound which holds ion carrier material are organic polymer compounds such as vinyl chloride resin, vinyl chloride-ethylene copolymer, polyester, polyacryl amide and polyurethane, and inorganic polymer compounds such as silicone resin. Vinyl chloride is especially preferred. Compounds are used in which the plasticizer does not readily elute. Examples of such a plasticizer are dioctyl sebacate ester, dioctyl adipate ester, dioctyl maleate ester and di-n-octyl phenylphosphonate. Dioctyl sebacate and di(2-ethylhexyl) sebacate are especially preferred.

Tetrahydrofuran (THF) is especially preferred for use as solvent. In order to coat the surface of the barrier layer with the ion-sensitive layer having the foregoing composition, the polymer compound, the plasticizer, the ion carrier material and the electrolytic salt are dissolved in a solvent (e.g. tetrahydrofuran). The electrically conductive substrate coated by the barrier layer is repeatedly dipped into the resulting solution followed by drying to adjust thickness. It is desired that the thickness of the applied ion-sensitive layer be 0.1 μm–10 mm, preferably 0.4–2.0 mm.

EXAMPLES 1–3

(1) A redox layer having a thickness of 30 μm was formed under the following conditions:

| 2,6-dimethylphenol | 0.5 M |
|---|---|
| sodium perchlorate | 0.2 M |
| solvent: acetonitrile | |

After the electrode potential was swept three times from 0 V to 1.5 V vs. a saturated sodium chloride saturated calomel electrode (SSCE) at a sweep rate of 50 mV/sec) under a temperature of −20° C., an electrolytic reaction was allowed to occur at 1.5 V for 10 min.

(2) A barrier layer having a thickness of 0.4 mm was formed of 10% PVA.

| Example 1 | No pH buffer solution |
|---|---|
| Example 2 | Buffer solution: Phosphate at pH 7.4 |
| Example 3 | Buffer solution: Chlorate at pH 5.6 |

(3) A 1.0 mm thick hydrogen ion-selective layer having the following composition was prepared:

| tridodecylamine | 10.0 mg/ml |
|---|---|
| tetrakis(p-chlorophenyl) potassium borate | 1.5 mg/ml |
| polyvinyl chloride ($P_n$ = 1050) | 81.2 mg/ml |
| dioctyl sebacate (DOS) | 160 mg/ml |
| solvent: tetrahydrofuran (THF) | 4 ml |

(Control)

As a control, a hydrogen ion sensor devoid of a barrier layer but having a redox layer and hydrogen ion-selective layer the same as those of Examples 1 through 3 was prepared.

(Experiment 1)

The hydrogen ion sensors fabricated in accordance with Examples 1–3 having the barrier layer between the redox layer and ion-selective layer were subjected to experimentation. Electromotive force with respect to a saturated sodium chloride saturated calomel electrode (SSCE) was plotted against pH using each hydrogen ion sensor as an active electrode and the SSCE as a reference electrode, and the dependence of the slope of the Nernst plot upon elapsed time was investigated to examine whether the substance constituting the redox layer eluted into the ion-selective layer. Dependence on oxygen gas concentration was investigated by determining the difference between potential measured after buffering nitrogen gas in a pH 7.4 phosphate buffer solution for 1 hr and potential measured after buffering oxygen gas in the phosphate solution for 1 hr, and comparing the differences among the ion sensors fabricated. Dependence on carbonic acid gas was investigated by dissolving carbon dioxide gas in a pH 7.4 phosphate buffer solution and observing any change in potential.

The characteristics of the control were also investigated in the same manner. The results of these experiments are as shown in Table 1 and FIG. 2.

EXAMPLES 4–7

Hydrogen ion sensors having the following barrier layers were fabricated as in Examples 1–3:

| Example 4 | pH buffer solution: phosphate at pH 4.5, thickness: 0.4 mm |
|---|---|
| Example 5 | pH buffer solution: phosphate at pH 4.5, thickness: 0.6 mm |
| Example 6 | pH buffer solution: citrate at pH 5.6, thickness: 0.4 mm |
| Example 7 | pH buffer solution: phosphate at pH 7.4, thickness: 0.4 mm |

(Experiment 2)

The pH-emf relations of the hydrogen ion sensors fabricated in accordance with Examples 4–7 were determined at temperatures of 20° C., 30° C., 37° C. and 45° C., and the slopes of the Nernst plot were investigated. It was also examined whether the redox layer composition eluted into the hydrogen-ion selective layer composition, and whether the hydrogen-ion selective layer composition eluted into the redox layer composition. The results are as shown in Table 2.

The results for each of the Examples 1–3 show that the slopes of the Nernst plot agree with the theoretical value of 61.55 mV/pH one day after the fabrication of the hydrogen ion sensor, and that there is almost no change in the plot slope for a period of three months, indicating that the value of slope is stable. The results also show no elution of redox layer composition into the hydrogen ion-selective layer composition, ad no elution of the hydrogen ion-selective layer composition into the redox layer composition. A 95% speed of response was found to be less than 5 sec.

The ion-selective layer was peeled off 90 days after fabrication of the inventive ion sensor and the layer was observed. Absolutely no change was observed in the color of the ion-selective layer that would have been caused by elution of a quinoid compound (reddish-brown in color) contained in the redox layer. On the other hand, it was observed that the ion-selective layer of the conventional ion sensor turned yellow about 20 days after fabrication. Other methods used to test for elution besides the visual examination method were spectral analysis (absorptiometry, etc.), gas chromatography and liquid chromatography. It will also be understood from the results that the hydrogen ion sensor of the invention is not influenced by oxygen gas or carbon dioxide It should be noted that the invention is not limited to the aforementioned examples thereof, and the compositions of the various layers are not limited to those set forth above.

A potassium ion sensor, sodium ion sensor, chlorine ion sensor and calcium ion sensor were also investigated as regards the characteristics of the slope of the Nernst plot, the occurrence of elution of the redox layer composition into the ion-selective layer composition, the elution of the ion-selective layer composition into the redox layer composition, as well as the dependence on oxygen gas and carbon dioxide. Results similar to those obtained with the hydrogen ion sensor were confirmed.

In Examples 4–7, the slopes (mV/pH) of the Nernst plot at 20° C.–45° C. approximate the theoretical value. It will be understood that since the isothermal point depends upon the pH range of 5–6, temperature dependence can be minimized in a pH range of 6.0–8.0, which is approximately the same as the pH range of a living body.

Results similar to those acquired in Examples 1–3 were obtained with regard to the occurrence of elution of the redox layer composition into the ion-selective layer composition and the elution of the ion-selective layer composition into the redox layer composition, though these results are not shown in Table 2. These results are ascribed to the fact that the barrier layer acts as an internal standard liquid layer in a conventional liquid membrane-type ion electrode, e.g. a glass electrode, owing to permeation of the barrier layer by the aqueous solution and resulting swelling of the barrier layer. These results were not obtained with a barrier layer having a thickness of less than 1 μm. Results similar to those obtained in Examples 4–7 were observed with regard to the potassium ion sensor, sodium ion sensor, chlorine ion sensor and calcium ion sensor.

The isothermal point can be set in any ionic concentration region by varying the ionic concentration of the barrier layer. This makes it possible to reduce temperature dependence in the range over which measurements are to be taken.

EXAMPLES 8–10

Hydrocarbon ion sensors having a barrier layer were fabricated.

(1) The redox layer was formed as in Examples 1–7. The barrier layer and hydrocarbon ion-selective layer also were formed as in Examples 1–7, though the layer compositions and thicknesses were changed as stated hereinbelow.

EXAMPLE 8

(2) Composition of barrier layer
10% PVA
sodium citrate at pH 5.6
0.01 M sodium bicarbonate
solvent: distilled water
barrier layer thickness: 0.2 mm
(3) Composition of hydrocarbon ion-selective layer
tridoctyl methyl ammonium salt 6 parts by weight
n-dodecyl alcohol 200 parts by weight
polyvinyl chloride ($P_n$ = 1050) 100 parts by weight
solvent: tetrahydrofuran (THF)
hydrocarbon ion-selective layer thickness: 0.8 mm

EXAMPLE 9

(2) Composition of barrier layer
10% PVA
0.1 M sodium chloride
0.01 M sodium bicarbonate
solvent: distilled water
barrier layer thickness: 0.4 mm
(3) Composition of hydrocarbon ion-selective layer
trioctyl methyl ammonium chloride 6 parts by weight
trichloroacetyl-p-butyl benzene 100 parts by weight
di(2-ethyl)hexyl sebacate 100 parts by weight
polyvinyl chloride ($P_n$ = 1050) 100 parts by weight
solvent: tetrahydrofuran (THF)
hydrocarbon ion-selective layer thickness: 1.0 mm

EXAMPLE 10

(2) Composition of barrier layer
10% PVA
solvent: distilled water
barrier layer thickness: 0.1 mm
(3) Composition of hydrocarbon ion-selective layer
trioctyl methyl ammonium salt 6 parts by weight
n-dodecyl alcohol 200 parts by weight
polyvinyl chloride ($P_n$ = 1050) 100 parts by weight
solvent: tetrahydrofuran (THF)
hydrocarbon ion-selective layer thickness: 1.0 mm (Control)

As a control, a hydrocarbon ion sensor devoid of a barrier layer but having a redox layer and hydrocarbon ion-selective layer the same as those of Example 10 was prepared.

(Experiment 3)

The hydrocarbon ion sensors fabricated in accordance with Examples 8–10 having the barrier layer between the redox layer and ion-selective layer were subjected to experimentation. Using the hydrocarbon ion sensor as the active electrode and a saturated sodium chloride saturated calomel electrode (SSCE) as the reference electrode, response of electromotive force was measured at 37° C. when a 0.1 mM sodium bicarbonate solution was titrated with a 0.5 M sodium bicarbonate solution to change the concentration. This was followed by investigating the influence on selectivity to anion, namely chlorine ion, perchloric acid ion, acetic acid ion and nitric acid solution. The influence from the concentration of oxygen in solution was examined over a period of 10 hr by measuring fluctuation in electromotive force.

The characteristics of the hydrocarbon ion sensor of the control were also investigated in the same manner. The results of these experiments are as shown in Tables 3 and 4 and in FIG. 3.

The results for each of the Examples 8–10 show that the slopes of the Nernst plot agree with the theoretical value of 61.55 mV/pH, and that there is almost no change in the plot slope for a period of three months, indicating that the value of slope is stable. The results also show substantially no elution of redox layer composition into the hydrocarbon ion-selective layer composition and of the hydrocarbon ion-selective layer composition into the redox layer composition. This was verified visually, by measuring a change in the intensity of ultraviolet spectrum absorption, and by liquid chromatography. Selectivity to chlorine ion, perchloric acid ion, acetic acid ion and nitric acid ion was excellent, and there was no influence from oxygen in solution. A 95% speed of response was found to be less than 1 min.

It should be noted that the invention is not limited to the aforementioned examples thereof, and the compositions of the various layers are not limited to those set forth above.

As many apparently widely different embodiments of the present invention can h=made without departing from the spirit and scope thereof it is to be understood that the invention is not limited to the specific embodiments thereof except as defined in the appended claims.

TABLE 1

|  | Examples | | | Control |
|---|---|---|---|---|
|  | 1 | 2 | 3 |  |
| (Redox Layer) Thickness | 30 μm | 30 μm | 30 μm | 30 μm |
| (Redox Layer Electrolyte Composition) | | | | |
| 2,6-dimethyl phenol | 0.5 M | 0.5 M | 0.5 M | 0.5 M |
| sodium perchlorate | 0.2 M | 0.2 M | 0.2 M | 0.2 M |
| (Solvent: Acetonitrile) | | | | |
| (Barrier Layer) Thickness | 0.4 mm | 0.4 mm | 0.4 mm | |
| (Barrier Layer Dipping Solution Composition) | 10% PVA | 10% PVA | 10% PVA | |
| buffer solution (pH) |  | Phosphate (7.4) | Citrate (5.6) | |
| (Solvent: Water) | | | | |
| (Hydrogen Ion-Selective Layer) Thickness | 1.0 mm | 1.0 mm | 1.0 mm | 1.0 mm |
| (Hydrogen Ion-Selective Layer Composition) | | | | |
| tridodecylamine | 10.0 mg/ml | 10.0 mg/ml | 10.0 mg/ml | 10.0 mg/ml |
| tetrakris(p-chlorophenyl) potassium borate | 1.5 mg/ml | 1.5 mg/ml | 1.5 mg/ml | 1.5 mg/ml |
| polyvinyl chloride (Pn = 1050) | 81.2 mg/ml | 81.2 mg/ml | 81.2 mg/ml | 81.2 mg/ml |
| dioctyl sebacate (DOS) | 160 mg/ml | 160 mg/ml | 160 mg/ml | 160 mg/ml |
| [Solvent: Tetrahydrofuran (THF) 4 ml] | | | | |
| (Nernst Plot Slope: mV/pH at 37° C.) | | | | |
| 1 Day After Fabrication | −53.4 | −61.0 | −61.0 | −61.0 |
| 30 Days After Fabrication | −61.3 | −61.6 | −61.4 | −60.5 |
| 60 Days After Fabrication | −61.4 | −60.6 | −61.2 | −59.5 |
| 90 Days After Fabrication | −61.5 | −60.8 | −61.6 | −58.5 |
| Elution of Redox Layer Composition into Hydrogen Ion-Selective Layer? | NO | NO | NO | YES |
| Elution of Hydrogen Ion-Selective Layer Composition into Redox Layer? | NO | NO | NO | YES |
| Oxygen Dependence | NO | NO | NO | YES |
| Carbon Dioxide Dependence | NO | NO | NO | YES |

TABLE 2

|  | Examples | | | |
|---|---|---|---|---|
|  | 4 | 5 | 6 | 7 |
| (Redox Layer) Thickness | 30 μm | 30 μm | 30 μm | 30 μm |
| (Redox Layer Electrolyte Composition) | | | | |
| 2,6-dimethyl phenol | 0.5 M | 0.5 M | 0.5 M | 0.5 M |
| sodium perchlorate | 0.2 M | 0.2 M | 0.2 M | 0.2 M |
| (Solvent: Acetonitrile) | | | | |
| (Barrier Layer) Thickness | 0.4 mm | 0.6 mm | 0.4 mm | 0.4 mm |
| (Barrier Layer Dipping Solution Composition) | 10% PVA | 10% PVA | 10% PVA | 10% PVA |
| buffer solution (pH) | Phosphate (4.5) | Phosphate (4.5) | Citrate (5.6) | Phosphate (7.4) |
| (Solvent: Water) | | | | |
| (Hydrogen Ion-Selective Layer) Thickness | 1.0 mm | 1.0 mm | 1.0 mm | 1.0 mm |
| (Hydrogen Ion-Selective Layer Composition) | | | | |
| tridodecylamine | 10.0 mg/ml | 10.0 mg/ml | 10.0 mg/ml | 10.0 mg/ml |
| tetrakris(p-chlorophenyl) potassium borate | 1.5 mg/ml | 1.5 mg/ml | 1.5 mg/ml | 1.5 mg/ml |
| polyvinyl chloride (Pn = 1050) | 81.2 mg/ml | 81.2 mg/ml | 81.2 mg/ml | 81.2 mg/ml |
| dioctyl debacate (DOS) | 160 mg/ml | 160 mg/ml | 160 mg/ml | 160 mg/ml |
| [Solvent: Tetrahydrofuran (THF) 4 ml] | | | | |
| (Nernst Plot Slope: mV/pH)a | | | | |
| 1 Day After Fabrication | | | | |
| 20° C. | −58.1 | −57.9 | −57.7 | −58.0 |
| 30° C. | −60.1 | −59.9 | −60.0 | −59.9 |
| 37° C. | −61.5 | −61.3 | −61.0 | −61.0 |
| 45° C. | −63.3 | −63.1 | −62.9 | −63.1 |
| 90 Days After Fabrication | | | | |
| 20° C. | −58.3 | −57.5 | −58.5 | −57.9 |
| 30° C. | −60.0 | −60.1 | −60.3 | −60.0 |
| 37° C. | −61.2 | −61.3 | −61.6 | −60.8 |
| 45° C. | −63.1 | −62.9 | −63.5 | −62.9 |

TABLE 3

|  | Examples | | | Control |
|---|---|---|---|---|
|  | 8 | 9 | 10 |  |
| (Barrier Layer) Thickness | 0.2 mm | 0.4 mm | 0.1 mm | |
| (Barrier Layer Dipping Solution Composition) | 10% PVA Sodium Citrate | 10% PVA 0.1 M NaCl | 10% PVA | |

TABLE 3-continued

|  | Examples | | | |
| --- | --- | --- | --- | --- |
|  | 8 | 9 | 10 | Control |
|  | (pH 5.6)<br>0.01 M NaHCO3 | 0.01 M NaHCO3<br>(Solvent: Distilled Water) | | |
| (Hydrocarbon-Ion Selective Layer) | | | | |
| Thickness | 0.8 mm | 1.0 mm | 1.0 mm | 1.0 mm |
| (Hydrocarbon-Ion Selective Layer Composition)? | | | | |
| trioctyl methyl ammonium salt | 6 parts by weight | | 6 parts by weight | 6 parts by weight |
| n-dodecyl alcohol | 200 parts by weight | | 200 parts by weight | 200 parts by weight |
| polyvinyl cholride (Pn = 1050) | 100 parts by weight | | 100 parts by weight | 100 parts by weight |
| trioctyl methyl ammonium chloride | | 3.4 parts by weight | | |
| trichloroacetyl-p-butyl benzene | | 100 parts by weight | | |
| di(2-ethyl)hexyl sebacate | | 100 parts by weight | | |
| polyvinyl chloride | | 100 parts by weight | | |
|  | [Solvent: Tetrahydrofuran (THF)] | | | |

TABLE 4

|  | Examples | | | |
| --- | --- | --- | --- | --- |
|  | 8 | 9 | 10 | Control |
| (Nernst Plot Slope: mV/pH at 37° C.) | | | | |
| 1 Day After Fabrication | 60.7 | 62.5 | 59.8 | 60.9 |
| 30 Days After Fabrication | 60.7 | 62.5 | 59.5 | 48.2 |
| 60 Days After Fabrication | 60.7 | 62.5 | 59.5 | — |
| 90 Days After Fabrication | 60.7 | 62.5 | 59.5 | — |
| Elution of Redox Layer Composition into Hydrocarbon Ion-Selective Layer? | NO | NO | NO | YES |
| Elution of Hydrocarbon Ion-Selective Layer Composition into Redox Layer Composition? | NO | NO | NO | YES |
| Ion Selectivity: $K^{Pa+}_{HCO_3-x-}$ | | | | |
| Chlorine Ion | $2.0 \times 10^{-2}$ | $2.5 \times 10^{-2}$ | $1.5 \times 10^{-2}$ | 0.01 |
| Perchlorate Ion | 6 | 8 | 4 | 0.7 |
| Acedic Acid ion | $4.5 \times 10^{-2}$ | $5 \times 10^{-2}$ | $3 \times 10^{-2}$ | 0.02 |
| Nitric Acid Ion | 0.1 | 0.3 | 0.05 | 0.09 |
| Oxygen Dependence? | NO | NO | NO | YES |

What is claimed is:

1. An ion sensor comprising:
   an electrically conductive substrate;
   a redox layer coating a surface of said electrically conductive substrate;
   a barrier layer coating a surface of said redox layer; and
   an ion-selective layer coating a surface of said barrier layer;
   said barrier layer made from a material which functions to prevent mutual contamination between said ion-selective layer and said redox layer with substances constituting these layers, and to transmit a potential produced in said ion-selective layer by contact with an ion from said ion-selective layer to said redox layer.

2. The ion sensor according to claim 1, wherein said material of the barrier layer is selected from a group consisting of a cellulose derivative, a natural aqueous polymer and a semisynthetic aqueous polymer.

3. The ion sensor according to claim 1, wherein said barrier layer has a thickness of 0.2 μm–1.0 mm.

4. The ion sensor according to claim 1, wherein said electrically conductive substrate is selected from a group consisting of an electrically conductive carbon material, a metal composite obtained by coating the surface of any of these metals with a semiconductor.

5. The ion sensor according to claim 4, wherein said carbon material comprises basal plane pyrolytic graphite or glassy carbon, said metal comprises gold, platinum, copper, silver, palladium or nickel and said semiconductor comprises iridium oxide or tin oxide.

6. The ion sensor according to claim 1, wherein said redox layer is selected from the group of materials having a redox function.

7. The ion sensor according to claim 1, wherein said redox layer is selected from the group of materials which undergo a quinone-hydroquinone type redox reaction.

8. The ion sensor according to claim 1, wherein said redox layer is selected from the group of materials which undergo an amine-quinoid type redox reaction.

9. The ion sensor according to claim 1, wherein said redox layer is selected from the group of electrically conductive materials consisting of poly (pyrrole) and poly(thienylene).

10. The ion sensor according to claim 1, wherein said redox layer has a thickness of from 0.01 μm to 1.0 mm.

11. The ion sensor according to claim 1, wherein said ion-sensitive layer has a thickness of from 1 μm to 10 mm.

12. The ion sensor according to claim 1, wherein said ion-sensitive layer comprises a polymeric membrane containing an ion carrier material, which is a compound expressed by the formula

where $R^1$, $R^2$, $R^3$ represent the same or different alkyl groups, among which at least two alkyl groups have a carbon number of 8–18, and is selective to hydrogen ion.

13. The ion sensor according to claim 1, wherein said ion-sensitive layer comprises an organic polymeric membrane containing a an ion carrier material, which is a compound expressed by the formula

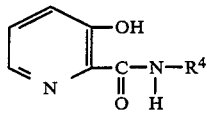

where $R^4$ represents an alkyl group having a carbon number of 8–18, and is selective to hydrogen ion.

14. The ion sensor according to claim 1, wherein said ion-sensitive layer comprises a polymeric membrane containing an ion carrier material, which is selected from the group consisting of valinomycin, nonactin, monactin, crown ether compounds, and is selective to potassium ion.

15. The ion sensor according to claim 14, wherein said crown either compound comprises dicyclohexyl-18-crown-6, naphto 15-crown-5 or bis(15-crown-5).

16. The ion sensor according to claim 1, wherein said ion-sensitive layer comprises a polymeric membrane containing an ion carrier material, which is selected from the group consisting of aromatic amides or diamides, aliphatic amides or diamides, and crown compounds, and is selective to sodium ion.

17. The ion sensor according to claim 1, wherein said ion-sensitive layer comprises a polymeric membrane containing an ion carrier material, which is selected from the group of quaternary ammonium salts expressed by the formula

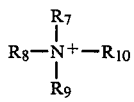

where $R^7$, $R^8$, $R^9$ represent the same or different alkyl groups which have a carbon number of 8–10, and $R_{10}$ represents hydrogen or an alkyl group having a carbon number of 1–8, and is selective to chloride ion.

18. The ion sensor according to claim 1, wherein said ion-sensitive layer comprises a polymeric membrane containing an ion carrier material comprising which is selected from triphenyl tin chloride, expressed by the formula

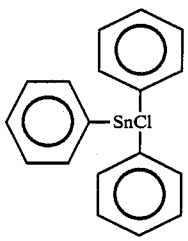

and is selective to chloride ion.

19. The ion sensor according to claim 1, wherein said ion-sensitive layer comprises a polymeric membrane containing an ion carrier material, which is selected from the group consisting of calcium bis(di-(n-octylphenyl) phosphate), (−)-(R,R)-N,N'-bis{(11-ethoxycarbonyl) undecyl}-N,N',4,5-tetramethyl-3,6-dioxaoctanediamide and calcium bis(di(n-decyl) phosphate), and is selective to calcium ion.

20. The ion sensor according to claim 1, wherein said ion-sensitive layer comprises a polymeric membrane containing an ion carrier material, which is selected from the group of quaternary ammonium salts expressed by the formula

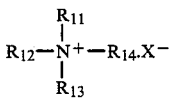

where $R_{11}$, $R_{12}$, $R_{13}$ represent the same or different alkyl groups having a carbon number of 8–18, $R^{14}$ represents hydrogen atom or an alkyl group having a carbon number of 1–4, and $X^-$ represents $Cl^-$, $Br^-$ or $OH^-$, and is selective to hydrogencarbonate ion.

21. The ion sensor according to claim 1, wherein said ion-sensitive layer comprises a polymeric membrane containing an ion carrier material, which is selected from the group of tertiary amine compounds expressed by the formula

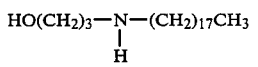

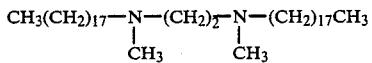

and is selective to hydrogencarbonate ion.

22. The ion sensor according to claim 1, wherein said ion-sensitive layer comprises a polymeric membrane containing an ion carrier material, which is selected from the group of nonactin consisting of monactin and tetranactin, and is selective to ammonium ion.

23. The ion sensor according to claim 1, wherein said ion-sensitive layer comprises an organic polymeric membrane containing an ion carrier material comprising N, N'-diheptyl-N,N'-dimethyl-1,4-butane diamide, and is selective to magnesium ion.

* * * * *